United States Patent [19]

Webster et al.

[11] Patent Number: 4,820,875

[45] Date of Patent: Apr. 11, 1989

[54] SYNTHESIS OF CARBONYL COMPOUNDS

[75] Inventors: Dennis E. Webster, Royston; Phillip J. Player, Hitchin, both of United Kingdom

[73] Assignee: Johnson Matthey Public Limited Company, London, United Kingdom

[21] Appl. No.: 137,001

[22] Filed: Dec. 23, 1987

[30] Foreign Application Priority Data

Dec. 23, 1986 [GB] United Kingdom ............... 86 30727

[51] Int. Cl.⁴ ............................................. C07C 45/39
[52] U.S. Cl. .................................. 568/360; 568/402; 568/471; 568/420
[58] Field of Search ............... 568/357, 360, 361, 401, 568/402, 420, 471

[56] References Cited

U.S. PATENT DOCUMENTS 3,794,221 8/1976 Duggan ............................... 568/357
4,250,121 2/1981 Mimouen ............................ 568/360

FOREIGN PATENT DOCUMENTS 0008013 7/1979 European Pat. Off. ............ 568/360

Primary Examiner—James H. Reamer
Attorney, Agent, or Firm—Cushman, Darby & Cushman

[57] ABSTRACT

In a process for vapour-phase synthesis of carbonyl compounds from alcohols a mixture of the alcohol and air or oxygen is passed over a silver catalyst. The concentration of alcohol:air or alcohol:oxygen is below the explosive limits. The process is conducted as a temperature between 200° and 450° C. Previously the production of carbonyl compounds required a temperature of 450°–700° C. which necessitated the use of heat exchangers using fused salt baths. The silver catalyst may be supported.

6 Claims, No Drawings

SYNTHESIS OF CARBONYL COMPOUNDS

This invention relates to a process for the vapour-phase synthesis of carbonyl compounds from alcohols.

One particular industrially-important carbonyl compound is cyclohexanone, used as a solvent and chemical intermediate, for example in the production of nylon. Cyclohexanone may be produced from cyclohexanol by dehydrogenation over a zinc, nickel or copper-based catalyst, but the reaction is endothermic and therefore commercially unfavourable. The reaction may, however, be rendered overall exothermic, and therefore commercially favourable, by adding oxygen (in the form of air or oxygen gas) to the cyclohexanol feed to react with the product hydrogen to form water. This reaction is known from, for example, European Patent Application No. 0008013, in which alcohols are oxidatively dehydrogenated to form carbonyl compounds in the presence of a silver and/or copper catalyst of specific particle size at a temperature of 450° to 700° C. In particular, cyclohexanol is reacted with air over a catalyst consisting of silver grains at a temperature of 600° C., to produce cyclohexanone at 88% of the theoretical yield. In this reaction, the concentration of cyclohexanol in the gases is 53% by volume, considerably above the explosive limits for cyclohexanol-air mixtures, which are believed to be 1–8% by volume. Furthermore, heat exchange at these high temperatures often necessitates the use of a heat transfer medium such as a fused salt bath. Such baths, however, are disadvantageous in that they tend to cause high levels of plant corrosion.

We have now found that oxidative dehydrogenation of alcohols to produce carbonyl compounds may be carried out at alcohol:oxygen (including alcohol:air) concentrations below the explosive limits, and at lower temperatures which avoid the use of fused salt baths.

According to the present invention, therefore, a process for the vapour-phase synthesis of carbonyl compounds from alcohols comprises passing a gaseous mixture containing the alcohol and oxygen over a catalyst comprising silver, in which the concentration of alcohol:oxygen is below the explosive limits.

Throughout this specification, references to "oxygen" are to be taken to include oxygen in the form of air or oxygen gas, and oxygen in admixture with another gas such as nitrogen, except where the context specifies otherwise.

By "explosive limits" is meant the experimentally-determined values, as these obviously vary according to the particular circumstances of the reaction, including the temperature and pressure at which the reaction is carried out and the concentration of oxygen used in this gas. For example, it is known that the lower explosive limit for a reaction in pure oxygen is slightly higher than that in air and the corresponding upper limit is substantially higher. Thus, for example, for methane the explosive limits in air are 5% (lower) and 15% (upper) whereas in oxygen they are 5.4% and 59.2%, respectively. Explosive limits for the corresponding alcohol in air and those for some other alcohols and cyclohexanone are shown below as examples:

| Alcohol | Explosive Limits (air) |
| --- | --- |
| $CH_3OH$ | 6.7–36.5%[1] |
| $C_2H_5OH$ | 3.28–18.95%[1] |
| $n-C_3H_7OH$ | 2.15–13.5%[1] |
| $i-C_3H_7OH$ | 2.02–11.8%[1] |
| $n-C_4H_9OH$ | 1.45–11.25%[1] |
| cyclohexanone | 1.1–8.1%[2] |

[1]Source: Handbook of Chemistry and Physics (64th Edition) published by CRC Press Inc.
[2]Source: Royal Society of Chemistry's Hazards in the Chemical Laboratory (3rd Edition), page 263.

The process according to the invention proceeds via oxidative dehydrogenation but at a markedly lower temperature than with prior art vapour phase processes. In particular, for the conversion of cyclohexanol to cyclohexanone, at a concentration of <1% by volume cyclohexanol in air, the reaction temperature is in the range 200°–450° C., preferably 250°–400° C., to give up to about 90% by weight conversion of cyclohexanol, at a selectivity to cyclohexanone of not less than about 97% by weight. The principal loss is by conversion to $CO_2$, which typically is present at only very low levels, for example not greater than 0.2% by volume, in the gas stream, above the input concentration. In contrast, at a concentration of cyclohexanol in air in excess of the explosive limits, only low conversions of cyclohexanol are obtained at a temperature of 320° C., temperatures of about 600° C. being required for economic conversion rates at these higher concentrations.

The ability to operate the process according to the invention at lower temperatures means that inert heat-exchange media such as "Dowtherm" (Registered Trade Mark) may be used.

The process according to the invention may be operated at a very slightly super-atmospheric pressure, for example from 0.01–0.35 kg cm$^{-2}$ above atmospheric pressure, preferably 0.03–0.14 kg cm$^{-2}$ above atmospheric pressure.

The silver catalyst may be silver metal in any convenient form, for example in the form of powder, grain, wire or gauze, or for reasons of economy may comprise silver or a silver-containing moiety dispersed on an inert support. The silver catalyst may optionally include a promoter material. The support is catalytically inert to prevent catalytic dehydration (for example of cyclohexanol to cyclohexene) from taking place. For this reason, high surface area catalyst supports are preferably avoided. More preferably, supports are selected from those having a surface area <200 m$^2$/g. Examples of suitable support materials include glass, α-alumina, silica, zinc oxide, tin oxide, chromia and metallic materials such as steel, copper, nickel and the like. As promoter material, we prefer to use an alkali metal or alkaline earth metal, or certain transition metals and metalloids. Examples of promoter materials include lithium, sodium, potassium, rubidium, caesium, magnesium, calcium, strontium, barium, copper, gold, iron, tin, nickel, manganese, molybdenum, zinc, palladium, antimony, bismuth and cobalt.

The process temperature may be controlled by preheating the inlet gas stream.

The invention will now be described by way of example for the conversion of cyclohexanol to cyclohexanone and of 1-octanol to 1-octanal, although a wide variety of alcohols or hydroxy-containing compounds are suitable for conversion to the corresponding carbonyl compound by the process according to the invention, such as alcohols having up to 10 carbon atoms, preferably alcohols having from 6 to 10 carbon atoms, but any alcohol which is in the vapour phase at the temperature of the reaction can be used.

In the examples, cyclohexanol feed was technical grade cyclohexanol containing, typically, 89% cyclohexanol, 6% cyclohexanone, balance inert constituents. T max is the maximum reactor temperature in °C., $\Delta T$ is the temperature difference between T max and the minimum temperature in the bed. A negative sign for $\Delta T$ implies an endotherm. The system was allowed to equilibrate at the respective temperature before being sampled.

Conversion in moles % is calculated from the gas chromatogram of the liquid product stream by $$\frac{\text{moles (reactant alcohol in)} - \text{moles (reactant alcohol out)}}{\text{moles (reactant alcohol in)}} \times 100$$

Selectivity in moles % is calculated from the same chromatogram by $$\frac{\text{moles (product aldehyde/ketone out)} - \text{moles (product in)}}{\text{moles (reactant alcohol in)} - \text{moles (reactant out)}} \times 100$$

In the examples, the reaction pressure was in the range 0.01–0.35 kg cm$^{-2}$ above atmospheric pressure, the precise value depending on the feed flow rate.

EXAMPLE 1A

Cyclohexanol was reacted with air over a catalyst consisting of 96.5 g silver grain of 3–7 mm size under the following conditions, the Table giving results at different temperatures:

| Bed volume: | 41.7 cm$^3$ | | |
|---|---|---|---|
| Gas flow rate: | 40 l min$^{-1}$ | | |
| Feed flow rate: | 75 g hr$^{-1}$ | | |
| Gas composition: | air | | |
| Vapour: gas ratio | 0.6% by volume | | |
| T max °C. | $\Delta T$ °C. | Conversion mole % | Selectivity mole % |
| 289 | −2 | 13 | 100.0 |
| 299 | +3 | 39 | 97.4 |
| 311 | +7 | 49 | 100.0 |
| 327 | +12 | 64 | 100.0 |
| 335 | +15 | 72 | 99.5 |
| 358 | +25 | 83 | 100.0 |

At a higher temperature of 380° C. the system was unstable and equilibration was not achieved.

EXAMPLE 1B

Comparative example at higher feed concentration outside the scope of this invention

| Feed: | cyclohexanol | | |
|---|---|---|---|
| Catalyst type: | silver grain 3–7 mm | | |
| Catalyst weight: | 98.8 g | | |
| Bed volume: | 41.7 cm$^3$ | | |
| Gas flow rate: | 2.5 l min$^{-1}$ | | |
| Feed flow rate: | 75 g hr$^{-1}$ | | |
| Gas composition: | air | | |
| Vapour: gas ratio | 10% by volume | | |
| T max °C. | $\Delta T$ °C. | Conversion mole % | Selectivity mole % |
| 288 | +26 | 2.4 | nc |
| 300 | +34 | 4.4 | nc |
| 316 | +47 | 8.0 | 100.0 |

-continued

| Feed: | cyclohexanol | | |
|---|---|---|---|
| Catalyst type: | silver grain 3–7 mm | | |
| Catalyst weight: | 98.8 g | | |
| Bed volume: | 41.7 cm$^3$ | | |
| Gas flow rate: | 2.5 l min$^{-1}$ | | |
| Feed flow rate: | 75 g hr$^{-1}$ | | |
| Gas composition: | air | | |
| Vapour: gas ratio | 10% by volume | | |
| T max °C. | $\Delta T$ °C. | Conversion mole % | Selectivity mole % |
| 326 | +57 | 12.4 | 100.0 |
| 349 | >75 | 19.8 | 100.0 |
| 410 | >120 | 33.5 | 100.0 |

(nc = not calculated)

At the temperatures of 349° C. and 410° C. the system was not stable. The temperature continued gradually to rise and the figures were calculated from spot samples taken at those temperatures. It can be seen that, at the vapour:gas ratio above the explosive limits, the conversion of alcohol to product is substantially less favourable than at vapour:gas ratios below the explosive limits.

EXAMPLE 2

Low density silver ribbon

| Feed: | cyclohexanol | | |
|---|---|---|---|
| Catalyst type: | melt-spun silver | | |
| Catalyst weight: | 21.08 g | | |
| Bed volume: | 41.7 cm$^3$ | | |
| Gas flow rate: | 25 l min$^{-1}$ | | |
| Feed flow rate: | 75 g hr$^{-1}$ | | |
| Gas composition: | air | | |
| Vapour: gas ratio | 1% by volume | | |
| T max °C. | $\Delta T$ °C. | Conversion % | Selectivity % |
| 311 | −3 | 16.9 | 100.0 |
| 327 | +9 | 33.5 | 100.0 |
| 356 | +29 | 54.4 | 99.4 |
| 360 | +34 | 61.1 | 99.8 |

At a higher temperature of 390° C. the system was unstable and did not equilibrate.

Examples 3 to 5 give results for silver catalysts deposited on a variety of different support materials.

EXAMPLE 3

| Feed: | cyclohexanol | | |
|---|---|---|---|
| Catalyst type: | 0.25% wt/wt Ag on 4 mm diameter glass beads | | |
| Catalyst weight: | 71.4 g | | |
| Bed volume: | 41.7 cm$^3$ | | |
| Gas flow rate: | 25 l min$^{-1}$ | | |
| Feed flow rate: | 75 g hr$^{-1}$ | | |
| Gas Composition: | 4% O$_2$ in N$_2$ | | |
| Vapour: gas ratio: | 1% by volume | | |
| T max °C. | $\Delta T$ °C. | Conversion mole % | Selectivity mole % |
| 325 | +15 | 58.0 | 100.0 |
| 353 | +27 | 77.4 | 97.9 |
| 380 | +38 | 87.1 | 97.0 |

The system was unstable at a temperature of 410° C.

EXAMPLE 4

| Feed: | cyclohexanol | | |
|---|---|---|---|
| Catalyst type: | 0.26% wt/wt Ag on 1-2 mm α-Al$_2$O$_3$ (Alcoa T60) | | |
| Catalyst weight: | 83.84 g | | |
| Bed volume: | 41.7 cm$^3$ | | |
| Gas flow rate: | 25 l min$^{-1}$ | | |
| Feed flow rate: | 75 g hr$^{-1}$ | | |
| Gas composition: | air | | |
| Vapour: gas ratio: | 1% by volume | | |
| T max °C. | ΔT °C. | Conversion mole % | Selectivity mole % |
| 264 | −15 | 1.7 | — |
| 284 | +1 | 24.4 | 97.5 |
| 320 | +24 | 58.0 | 98.0 |
| 355 | +55 | 73.0 | 97.8 |

At temperatures above 355° C. the % conversion began to decrease and the system was unstable at a temperature of 405° C.

EXAMPLE 5

| Feed: | cyclohexanol | | |
|---|---|---|---|
| Catalyst type: | 3.5% wt/wt Ag on "304" stainless steel pad. | | |
| Catalyst weight: | 28.4 g | | |
| Bed volume: | 41.7 cm$^3$ | | |
| Gas flow rate: | 25 l min$^{-1}$ | | |
| Feed flow rate: | 75 g hr$^{-1}$ | | |
| Gas composition: | air | | |
| Vapour: gas ratio: | 1% by volume | | |
| T max °C. | ΔT °C. | Conversion mole % | Selectivity mole % |
| 287 | +4 | 8.4 | 98.6 |
| 322 | +20 | 24.1 | 98.5 |
| 349 | +36 | 44.4 | 98.6 |
| 360 | +46 | 53.0 | 98.9 |
| 371 | +51 | 55.8 | 99.8 |

The system was unstable at a temperature of 410° C.

EXAMPLE 6

Use of Octanol as Feed

| Feed: | 1-octanol (G.P.R. grade) | | |
|---|---|---|---|
| Catalyst type: | silver grain 3-7 mm | | |
| Catalyst weight: | 98.8 g | | |
| Bed volume: | 41.7 cm$^3$ | | |
| Gas flow rate: | 25 l min$^{-1}$ | | |
| Feed flow rate: | 75 g hr$^{-1}$ | | |
| Gas composition: | air | | |
| Vapour: gas ratio: | 0.8% by volume | | |
| T max °C. | ΔT °C. | Conversion mole % | Selectivity mole % |
| 289 | +10 | 35.4 | 100.0 |
| 299 | +20 | 40.0 | 100.0 |
| 326 | +41 | 54.7 | 98.0 |

The system was unstable at a temperature of 358° C.

We claim:

1. In the process for the vapour-phase synthesis of an aldehyde or ketone product from an alcohol of 6 to 10 carbon atoms, the improvement comprising passing a gaseous mixture containing the alcohol and oxygen over a catalyst comprising metallic silver, in which the concentration of alcohol:oxygen is below the lower explosive limit and the reaction temperature is in the range of 200° to 450° C.

2. The process of claim 1, in which the reaction temperature is in the range of 250°–400° C.

3. The process of claim 1, in which the reaction pressure is in the range of 0.01–0.35 kg cm$^{-2}$ above atmospheric pressure.

4. The process of claim 1, in which the silver metal is present in the form of silver gauze.

5. The process of claim 1, in which the catalyst comprises metallic silver dispersed on an inert support.

6. The process of claim 1, in which the alcohol comprises cyclohexanol and the product comprises cyclohexanone.

* * * * *